United States Patent
Shanahan et al.

(10) Patent No.: US 9,604,983 B2
(45) Date of Patent: Mar. 28, 2017

(54) HERBICIDAL 3-(2-BENZYLOXYPHENYL)-2,4-DIHYDROXY-1,8-NAPHTHYRIDINE DERIVATIVES

(71) Applicant: SYNGENTA LIMITED, Guildford, Surrey (GB)

(72) Inventors: Stephen Edward Shanahan, Bracknell (GB); Alan Joseph Hennessy, Bracknell (GB); Timothy Jeremiah Cornelius O'Riordan, Bracknell (GB); Paul Matthew Burton, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 15/032,095

(22) PCT Filed: Oct. 24, 2014

(86) PCT No.: PCT/EP2014/072831
§ 371 (c)(1),
(2) Date: Apr. 26, 2016

(87) PCT Pub. No.: WO2015/062984
PCT Pub. Date: May 7, 2015

(65) Prior Publication Data
US 2016/0304509 A1    Oct. 20, 2016

(30) Foreign Application Priority Data

Nov. 1, 2013 (GB) .................................. 1319411.3

(51) Int. Cl.
*C07D 471/04* (2006.01)
*A01N 43/90* (2006.01)

(52) U.S. Cl.
CPC .......... *C07D 471/04* (2013.01); *A01N 43/90* (2013.01)

(58) Field of Classification Search
None
See application file for complete search history.

(56) References Cited

FOREIGN PATENT DOCUMENTS

| WO | 2008009908 A1 | 1/2008 |
|---|---|---|
| WO | 2008071918 A1 | 6/2008 |
| WO | 2009063180 A1 | 5/2009 |
| WO | 2009090401 A2 | 7/2009 |
| WO | 2012028580 A1 | 3/2012 |

OTHER PUBLICATIONS

International Search Report for International Patent Application No. PCT/EP2014/072831 mailed Nov. 27, 2014.

*Primary Examiner* — Abigail Fisher
*Assistant Examiner* — Frank Choi
(74) *Attorney, Agent, or Firm* — James Cueva

(57) ABSTRACT

The present invention relates to herbicidal benzyloxy-substituted phenyl-diones and phenyl-dioxo-thiazinones of formula (I), as well as to herbicidal compositions comprising such compounds, and to the use of such compounds or compositions in controlling undesirable plant growth, in particular in controlling weeds, such as broad-leaved dicotyledonous weeds, in crops of useful plants. Formula (I), or a salt or N-oxide thereof, wherein $A_1$ is N or $CR^1$; $A_3$ is C(O) or $S(O)_2$; G is hydrogen or $C(O)R^6$; $R^1$, $R^3$, X and Y are i.a. hydrogen, alkyl or haloalkyl; n is 0-5; each Z is i.a. alkyl, haloalkyl or alkoxy; and $R^6$ is i.a. alkyl, alkenyl or alkynyl.

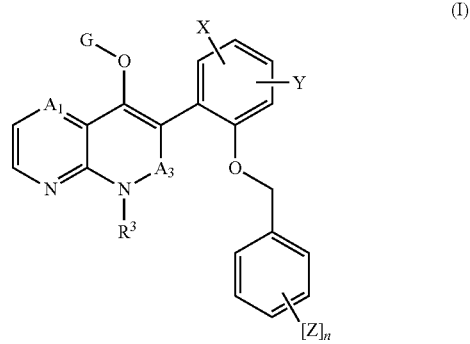

14 Claims, No Drawings

HERBICIDAL 3-(2-BENZYLOXYPHENYL)-2,4-DIHYDROXY-1,8-NAPHTHYRIDINE DERIVATIVES

RELATED APPLICATION INFORMATION

This application is a 371 of International Application No. PCT/EP2014/072831, filed Oct. 24, 2014, which claims priority to GB Application No. 1319411.3, filed Nov. 1, 2013, the contents of which are incorporated herein by reference herein.

The present invention relates to herbicidal benzyloxy-substituted phenyl-diones and benzyloxy substituted phenyl-dioxo-thiazinone derivatives of formula (I), as well as to processes and intermediates used for the preparation of such derivatives. The invention further extends to herbicidal compositions comprising such derivatives, as well as to the use of such compounds and compositions in controlling undesirable plant growth: in particular the use in controlling weeds, such as broad-leaved dicotyledonous weeds, in crops of useful plants.

Both WO 2008/009908 and WO 2008/071918 describes pyridopyrazine derivatives with herbicidal utility, as well as processes for their preparation and compositions comprising them, whilst WO 2009/090401 discloses herbicidal compositions comprising pyridopyridines, pyridodiazines and pyridotriazines.

WO 2009/063180 relates to 1H-2-thia-1,5,8-triazanaphthalene-2,2-dioxides, and their use in controlling plants or in inhibiting plant growth and WO 2012/028580 describes herbicidally active pyridylketosultams.

The present invention is based on the finding that benzyloxy-substituted phenyl-diones and benzyloxy substituted phenyl-dioxo-thiazinone derivatives of formula (I), exhibit surprisingly good herbicidal activity.

Thus, in a first aspect there is provided a compound of formula (I)

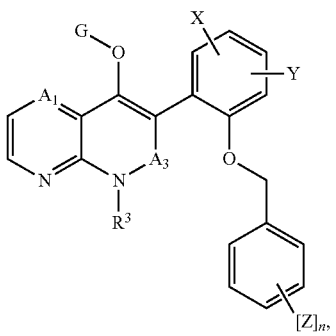

(I)

or a salt or N-oxide thereof, wherein $A_1$ is N or $CR^1$; $R^1$ is hydrogen, $C_1$-$C_4$alkyl, $C_1$-$C_4$haloalkyl, $C_1$-$C_4$alkoxy, $C_1$-$C_4$alkylthio, halogen, cyano, hydroxyl, or phenyl optionally substituted by one to five $R^4$ which may be the same or different; $A_3$ is C(O) or S(O)$_2$; G is hydrogen, or C(O)$R^6$; X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen; n is an integer of 0, 1, 2, 3, 4, or 5; each Z is independently $C_1$-$C_3$ alkyl, $C_1$-$C_3$ alkoxy, $C_1$-$C_3$haloalkyl, $C_1$-$C_3$haloalkoxy, or halogen; $R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N-$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{10}$, which may be the same or different, or heterocyclyl-$C_1$-$C_6$alkyl- or heterocyclyl-$C_1$-$C_6$alkyl- wherein the heterocyclyl moiety is substituted by one to three $R^{10}$, which may be the same or different; each $R^4$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, or $C_1$-$C_{10}$alkylcarbonylamino-; $R^6$ is selected from the group consisting of $C_1$-$C_6$alkyl, $C_1$-$C_6$alkenyl, $C_1$-$C_6$alkynyl, $C_1$-$C_6$alkyl-S—, —NR$^7$R$^8$ and phenyl optionally substituted by one or more $R^9$; $R^7$ and $R^8$ are independently selected from the group consisting of $C_1$-$C_6$ alkyl and $C_1$-$C_6$ alkoxy, or $R^7$ and $R^8$ together can form a morpholinyl ring; $R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and, each $R^{19}$ is independently halo, $C_1$-$C_4$alkyl, $C_1$-$C_4$haloalkyl, $C_1$-$C_4$alkoxy or $C_1$-$C_4$haloalkoxy.

Compounds of formula (I) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are di-substituted alkenes, these may be present in (E)- or (Z)-form or as mixtures of both in any proportion.

Furthermore, compounds of formula (I) may be in equilibrium with alternative tautomeric forms. For example, a compound of formula (I-i), i.e. a compound of formula (I) wherein $R^3$ is hydrogen, $A_3$ is C(O) and G is hydrogen, can be drawn in at least five tautomeric forms:

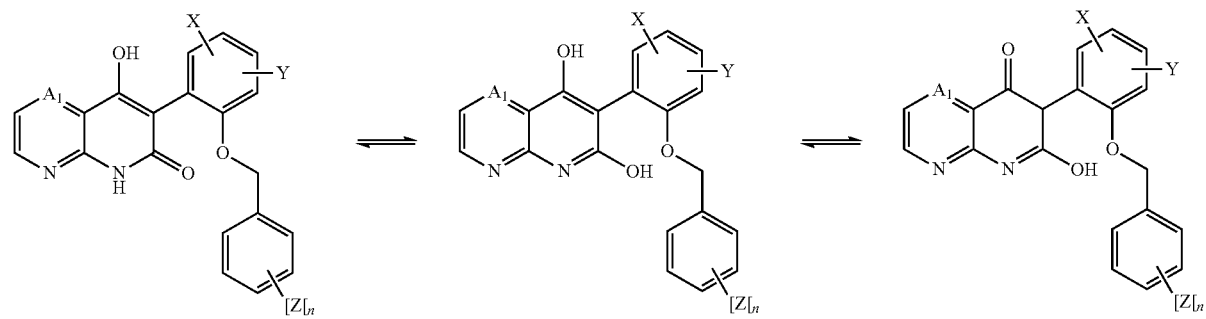

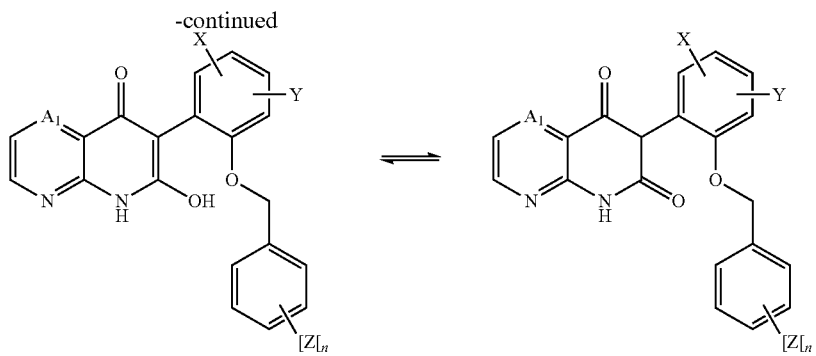

Similarly, a compound of formula (I-ii), i.e. a compound of formula (I) wherein $A_3$ is $S(O)_2$ and G is hydrogen, can be drawn in two tautomeric forms:

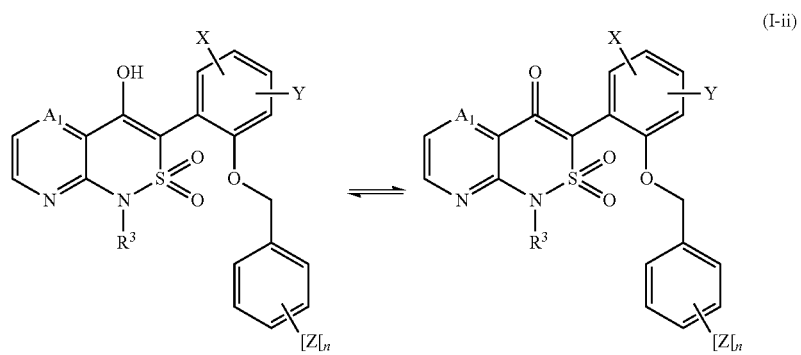

(I-ii)

It should be appreciated that all tautomeric forms (single tautomer or mixtures thereof), racemic mixtures and single isomers are included within the scope of the present invention.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups (such as methyl).

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Preferably, the term cycloalkyl refers to cyclopropyl, cyclobutyl, cyclopentyl or cyclohexyl.

In the context of the present specification the term "aryl" preferably means phenyl. The term "heteroaryl" as used herein means an aromatic ring system containing at least one ring heteroatom and consists of a single ring. Preferably, single rings will contain 1, 2 or 3 ring heteroatoms selected independently from nitrogen, oxygen and sulfur. Typically "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, or 1,3,5-triazinyl.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur. Examples of heterocyclic groups include oxetanyl, thietanyl, azetidinyl and 7-oxa-bicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The present invention also includes agronomically acceptable salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used. The compounds of formula (I) according to the invention also include hydrates which may be formed during the salt formation.

Preferred values of $A_1$, $A_3$, $R^1$, $R^3$, $R^4$, $R^6$, $R^7$, $R^8$, $R^9$, $R^{10}$, G, X, Y, Z, and n are as set out below, and a compound of formula (I) according to the invention may comprise any combination of said values. The skilled man will appreciate that values for any specified set of embodiments may combined with values for any other set of embodiments where such combinations are not mutually exclusive.

As defined above, $A_1$ is N or $CR^1$. In one set of embodiments, $A_1$ is N. In a further set of embodiments, $A_1$ is $CR^1$.

Where $A_1$ is $CR^1$ and $R^1$ is phenyl optionally substituted by one to five $R^4$, preferably each $R^4$ is independently halo, $C_1$-$C_4$alkyl, $C_1$-$C_4$haloalkyl, $C_1$-$C_4$alkoxy, or $C_1$-$C_4$haloalkoxy. Preferred groups for $R^4$ are chloro, fluoro, methyl, ethyl, trifluoromethyl, methoxy or trifluoromethoxy.

However, where $A_1$ is $CR^1$, it is preferred that $R^1$ is selected from the group consisting of hydrogen, halogen, cyano, hydroxyl, $C_1$-$C_3$alkyl, $C_1$-$C_3$alkoxy. More preferably $R^1$ is hydrogen, halogen, $C_1$-$C_3$alkyl, $C_1$-$C_3$alkoxy, and even more preferably hydrogen, chlorine, bromine, methyl, or methoxy.

In one set of embodiments $R^1$ is hydrogen, methyl, or methoxy. In a further set of embodiments $R^1$ is hydrogen, or methoxy.

As stated herein, $A_3$ is either C(O) or S(O)$_2$. In one set of preferred embodiments $A_3$ is C(O).

Preferably $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl. Examples of such preferred groups for $R^3$ are hydrogen, methyl, ethyl, n-propyl, iso-propyl, n-butyl, 2-methyl-propyl, 2-fluoro-ethyl, 2,2-difluoro-ethyl, 2,2,2-trifluoro-ethyl, allyl, but-3-en-1-yl or propargyl.

More preferably $R^3$ is hydrogen, $C_1$-$C_2$alkyl, $C_1$-$C_2$haloalkyl, $C_2$-$C_3$alkenyl or $C_2$-$C_3$alkynyl. Examples of such more preferred groups for $R^3$ are hydrogen, methyl, ethyl, 2,2-difluoro-ethyl, 2,2,2-trifluoro-ethyl, allyl or propargyl.

Most preferably $R^3$ is hydrogen, $C_1$-$C_2$alkyl, $C_1$-$C_2$haloalkyl or $C_2$-$C_3$alkynyl. Examples of such most preferred groups for $R^3$ are hydrogen, methyl, ethyl, 2,2-difluoro-ethyl or propargyl, with 2,2-difluoro-ethyl and propargyl being particularly preferred.

As described herein, G may be hydrogen or —C(O)—$R^6$, and $R^6$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —$NR^7R^8$ and phenyl optionally substituted by one or more $R^9$. As defined herein, $R^7$ and $R^8$ are independently selected from the group consisting of $C_1$-$C_6$ alkyl, $C_1$-$C_6$ alkoxy-; or they can together form a morpholinyl ring. Preferably $R^7$ and $R^8$ are each independently selected from the group consisting of methyl, ethyl, propyl, methoxy, ethoxy and propoxy. $R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy.

Preferably $R^6$ is $C_1$-$C_4$ alkyl, $C_2$-$C_3$alkenyl, $C_2$-$C_3$alkynyl, —$C_1$-$C_3$alkoxy, or —$NR^7R^8$ wherein $R^7$ and $R^8$ together form a morpholinyl ring. More preferably $R^6$ is isopropyl, t-butyl, methyl, ethyl, propargyl or methoxy.

In one set of embodiments G is hydrogen or —C(O)—$R^6$, wherein $R^6$ is $C_1$-$C_4$ alkyl, $C_2$-$C_3$alkenyl, $C_2$-$C_3$alkynyl or —$C_1$-$C_3$alkoxy. In a further set of embodiments G is hydrogen or —C(O)—$R^6$, wherein $R^6$ is isopropyl, t-butyl, methyl, ethyl, propargyl or methoxy. However, it is particularly preferred that G is hydrogen.

X is preferably hydrogen or halogen, more preferably hydrogen, fluorine, chlorine, or bromine. More preferably still, hydrogen, fluorine or chlorine.

In one set of embodiments it is preferred that X is ortho with respect to the bi-cyclic moiety. It is particularly preferred that X is either fluorine or chlorine and is ortho with respect to the bi-cyclic moiety.

Y is preferably hydrogen, $C_1$-$C_3$ alkyl, $C_1$-$C_3$haloalkyl, or halogen.

In one set of embodiments it is preferred that Y is ortho with respect to the benzyloxy moiety. It is particularly preferred that Y is ortho with respect to the benzyloxy moiety and is halogen, in particular chlorine.

As described herein, Z may be $C_1$-$C_3$ alkyl, $C_1$-$C_3$ alkoxy, $C_1$-$C_3$haloalkyl, $C_1$-$C_3$haloalkoxy, or halogen and n is an integer of 0, 1, 2, 3, 4, or 5. Accordingly, the benzyl moiety of formula (I) may be represented as follows wherein p denotes the point of attachment to the remainder of the molecule via the ether link:

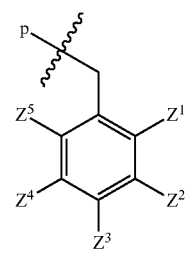

Preferably each Z radical is independently selected from halogen (in particular chlorine), methyl, methoxy, trifluoromethyl and trifluoromethoxy. More preferably each Z radical is independently selected from halogen (in particular chlorine), methyl, methoxy, and trifluoromethoxy. Equally preferably, each Z radical is independently selected from halogen (in particular chlorine), methyl, methoxy and trifluoromethyl.

It is preferred that n is 0, 1, or 2, more preferably 0 or 1. Where n is 1, it is preferred that Z is para with respect to the methoxy linker (i.e. Z is at position $Z^3$). Where n is 2, it is preferred that one substituent will be para and the other will be meta with respect to the methoxy linker (i.e. one Z radical will be at position $Z^2$ or $Z^4$, and the other Z radical will be at position $Z^3$). In one particularly preferred set of embodiments n is 0 (i.e. positions $Z^1$, $Z^2$, $Z^3$, $Z^4$ and $Z^5$ all carry hydrogen). In a further particularly preferred set of embodiments n=1.

In one particularly preferred set of embodiments $A_1$ is CH, C-methoxy, or N (preferably CH or C-methoxy), G is H or —C(O)-isopropyl, $R^3$ is propargyl or difluoroethyl, X and Y are each independently halogen (more preferably chloro), n is 0, 1 or 2 and each Z is independently halogen (preferably chloro), methoxy, or trifluoromethoxy.

In one particularly preferred set of embodiments $A_1$ is CH, C-methoxy, or N (preferably CH or C-methoxy), G is H or —C(O)-isopropyl, $R^3$ is propargyl or difluoroethyl, X is hydrogen or halogen (in particular hydrogen, chloro, or fluoro), Y is halogen (in particular chloro), n is 0, 1, or 2, and where n is greater than 0, each Z is independently halogen (preferably chloro), methyl, methoxy, or halomethyl (preferably trifluoromethyl).

In a further more particularly preferred set of embodiments, $A_1$ is CH or C-methoxy, G is H or —C(O)-isopropyl, $R^3$ is propargyl or difluoroethyl, X is hydrogen, chloro, or fluoro, Y is chloro, n is 0, or 1, and where n is 1, Z is para with respect to the methoxy linker (i.e. be at position $Z^3$) and will be chloro, methyl, methoxy, or trifluoromethyl.

The compounds of the present invention may be prepared according to the following schemes, in which the substituents $A_1$, $R^3$, $A_3$, G, X, Y, Z and n have (unless otherwise stated explicitly) the definitions described hereinbefore.

Certain compounds of the present invention, e.g of formula (1a), may be prepared from compounds of formula (1b) (also compounds of the invention) as shown in Reaction scheme 1.

Reaction scheme 1

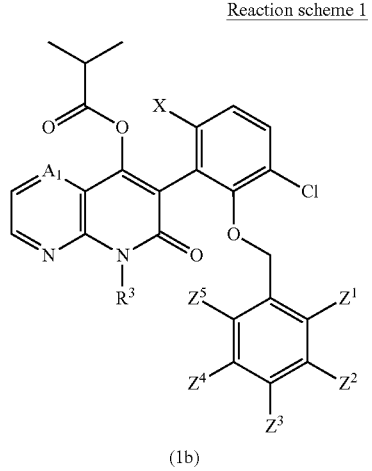

(1b)

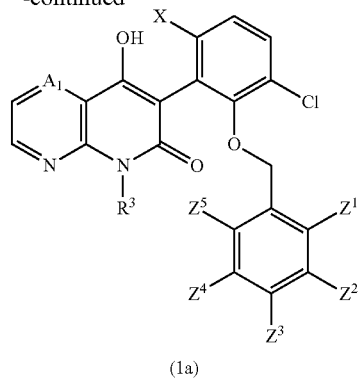

(1a)

Compounds of formula (1a) (in which $A_1$ is N, C(H) or C(OMe), $R^3$ is —CH$_2$C≡CH or —CH$_2$CHF$_2$, X is H, Cl or F, and $Z^1$ to $Z^5$ are each independently hydrogen or as defined hereinbefore for Z), may be prepared by treatment of ester compounds (1b) (in which $A_1$ is N, C(H) or C(O)Me, $R^3$ is —CH$_2$C≡CH or —CH$_2$CHF$_2$, and $Z^1$ to $Z^5$ are each independently hydrogen or as defined hereinbefore for Z) with NaOH or KOH in aqueous THF, at a temperature between 20 and 100° C.

Compounds of formula (1b) may be prepared from compounds of formula (2) (wherein $A_1$, $R^3$, X and $Z^1$ to $Z^5$ are as defined in Reaction scheme 1) as shown in Reaction scheme 2 below.

Reaction scheme 2

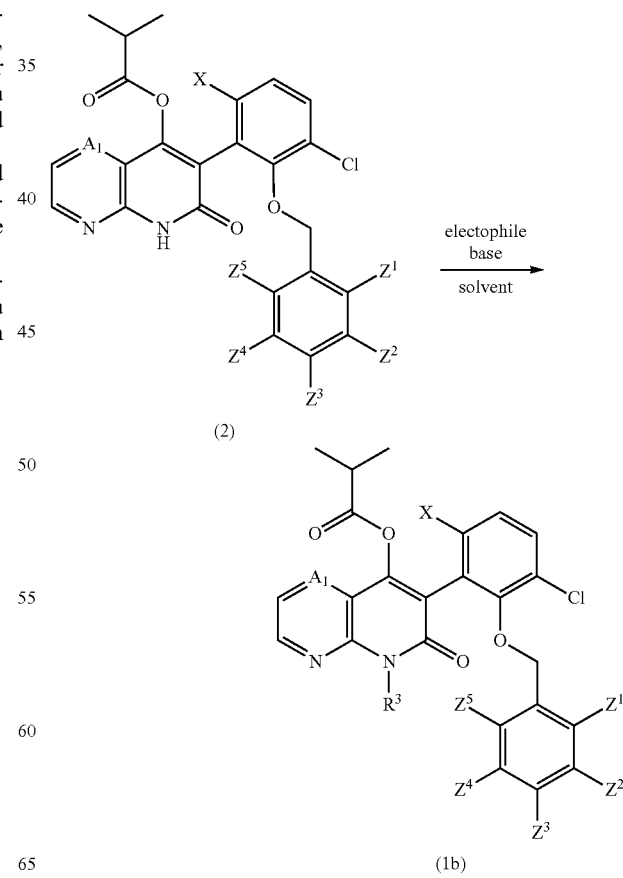

Compounds of formula (1b) may be prepared by N-alkylation of heterocycles (2) with an electrophilic alkylating agent, in the presence of a suitable base and solvent, at a temperature between 0 and 25° C. Examples of suitable electrophile reagents are propargyl bromide or 2,2-difluoroethyl triflate. Examples of suitable bases are NaH or diisopropylethylamine, and of suitable solvents are THF, acetonitrile or DMF (N,N-dimethylformamide).

Compounds of formula (2) may be prepared by acylation of compounds (3) as shown in Reaction scheme 3 below.

Reaction scheme 3

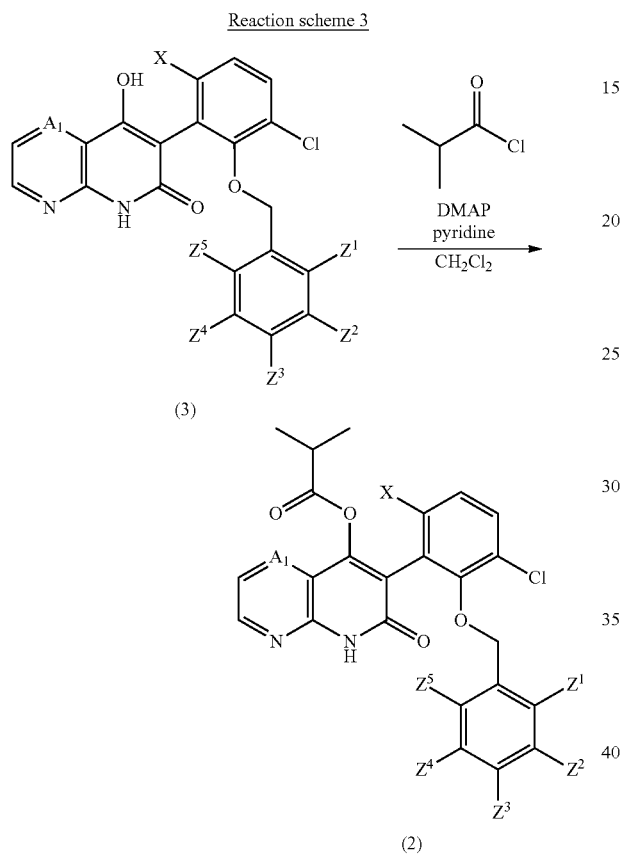

(3)

(2)

wherein $A_1$ is N, C(H) or C(OMe), and X and $Z^1$ to $Z^5$ are as defined above in Reaction scheme 1. DMAP is 4-(Dimethylamino)pyridine, a substoichiometric catalyst.

Compounds of formula (3) may be prepared by cyclization of amides (4) as shown in Reaction scheme 4 below.

Reaction scheme 4

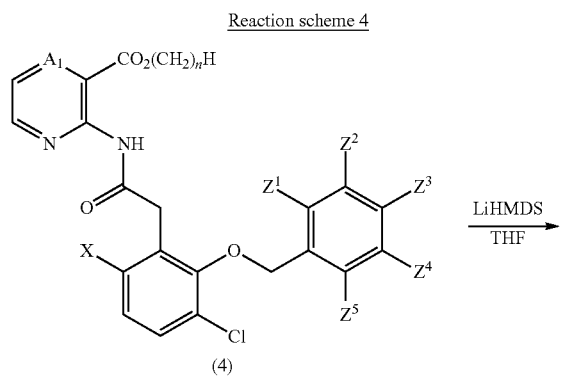

(4)

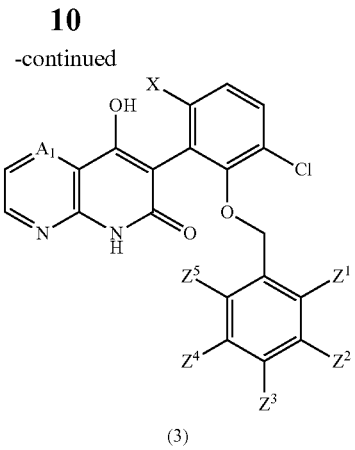

(3)

wherein $A_1$ is N, C(H) or C(OMe), and X and $Z^1$ to $Z^5$ are as defined above in Reaction scheme 1, and n is 1 or 2.

Compounds of formula (4) may be prepared by amide coupling of amino-heterocycles (5) with phenylacetic acids (6) as shown in Reaction scheme 5.

Reaction scheme 5

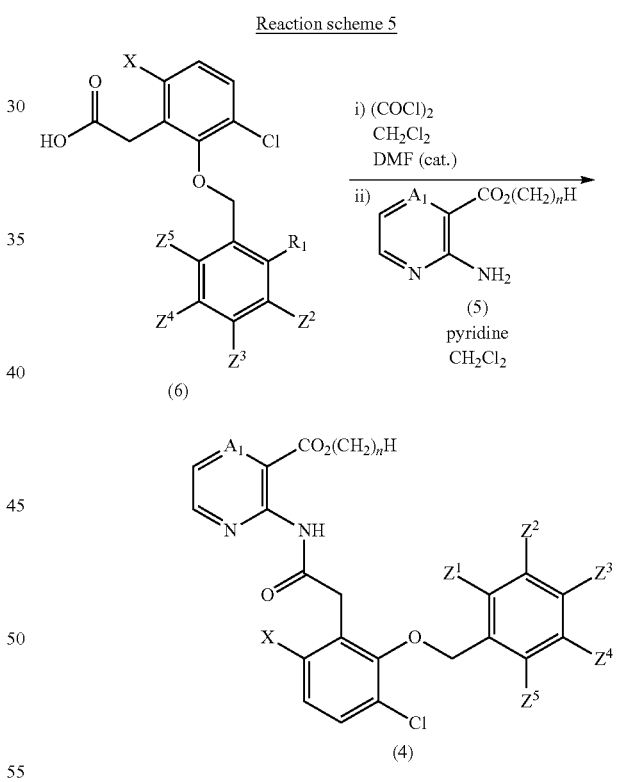

(4)

wherein $A_1$, X and $Z^1$ to $Z^5$ are as defined above in Reaction scheme 1, and n is 1 or 2.

With reference to Reaction scheme 5, an example of an amino-heterocycle (5) is commercially available 2-aminonicotinic acid ethyl ester. A further example of compound of formula (5) is methyl 3-aminopyrazine-2-carboxylate, prepared according to WO2005115986(A1), 2005 or U.S. Pat. No. 5,252,538 A1, 1993. A further example of compound of formula (5) is ethyl 2-amino-4-methoxy-pyridine-3-carboxylate, prepared as shown in Reaction scheme 6 below.

Reaction scheme 6

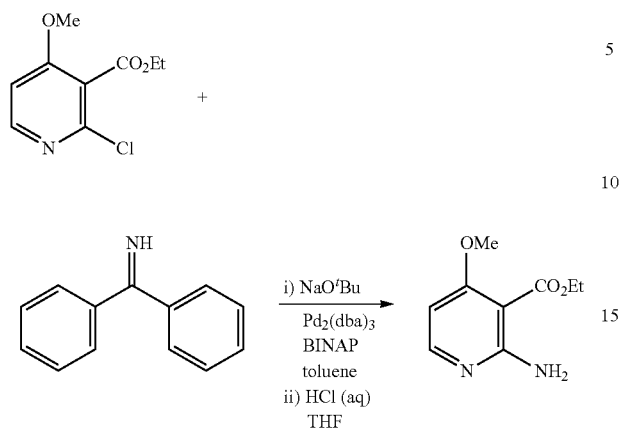

With reference to Reaction scheme 6, ethyl 2-chloro-4-methoxy-pyridine-3-carboxylate can be prepared according to *J. Org. Chem.*, 2005, 70, 6204, and benzophenone-imine is readily available from a variety of commercial sources Compounds of formula (6) may be prepared by oxidation of olefins (7) according to Reaction scheme 7.

Reaction scheme 7

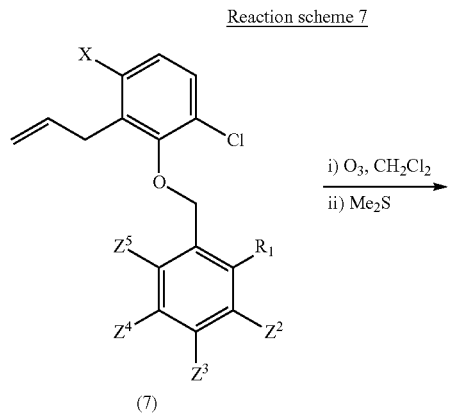

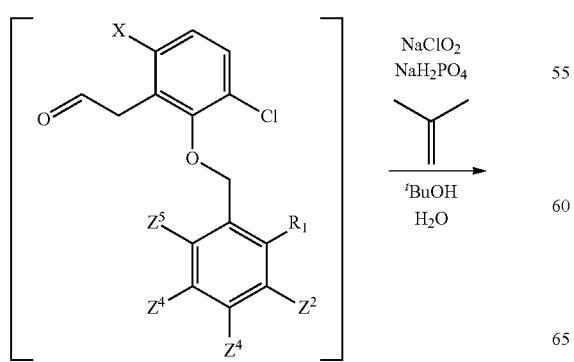

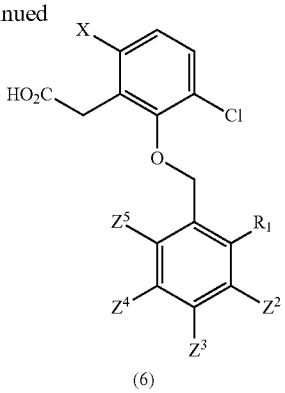

(6)

wherein X and $Z^1$ to $Z^5$ are as defined above in Reaction scheme 1.

Olefin compounds (7) may be prepared by the O-alkylation of phenols (8) with a benzyl halide compound, as shown in Reaction scheme 8.

Reaction scheme 8

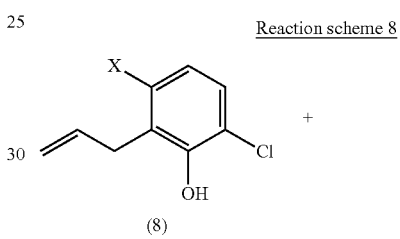

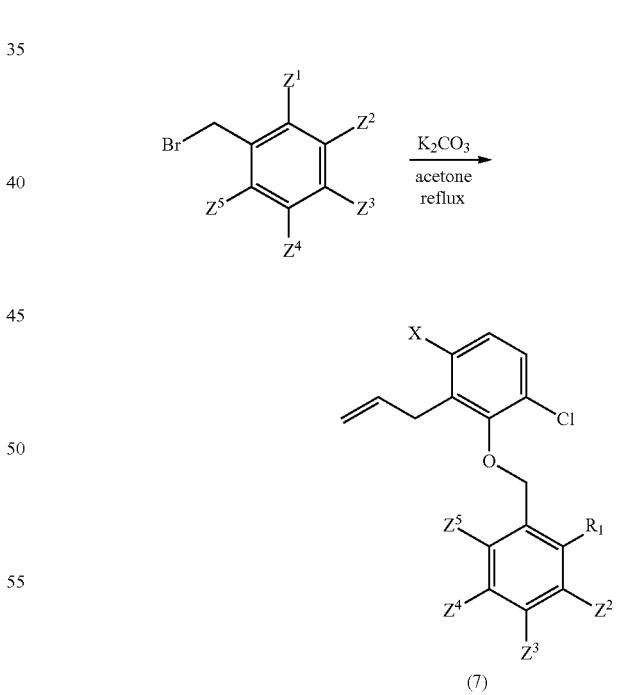

wherein X and $Z^1$ to $Z^5$ are as defined above in Reaction scheme 1.

With reference to Reaction scheme 8, many benzyl halides are commercially available, e.g. benzyl bromide. Phenols (8) may be prepared as shown in Reaction scheme 9 below.

Reaction scheme 9

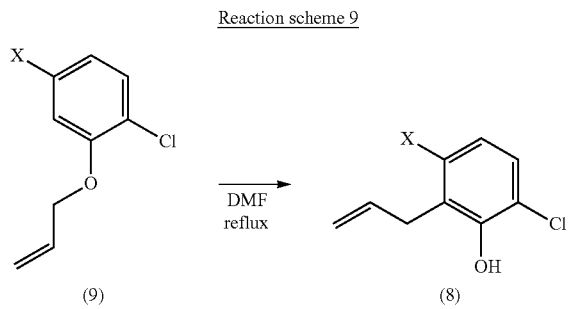

wherein X is as defined above in Reaction scheme 1.

Phenols (8) may be prepared by thermal rearrangement of allyl ether compounds (9) as shown in Reaction scheme 9. An example of an ether (9) is 2-allyloxy-1,4-dichlorobenzene, which may be prepared according to *J. Chem. Soc., Perkin Trans.* 2, 2001, 1824.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilizers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurized, hand-actuated spray pumps.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of Formula (I) and, optionally, a carrier or diluent therefore. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominantly mono-esters) or phosphorus pentoxide (predominantly di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacetmethyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6).

The compounds of the present invention may also be combined with herbicidal compounds disclosed in WO06/024820 and/or WO07/096576.

The mixing partners of the compound of Formula (I) may also be in the form of esters or salts, as mentioned e.g. in The Pesticide Manual, Fourteenth Edition, British Crop Protection Council, 2006.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula (I) according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxybenzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to overexpress homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavor).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled include both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

Various aspects and embodiments of the present invention will now be illustrated in more detail by way of example. It will be appreciated that modification of detail may be made without departing from the scope of the invention.

PREPARATION EXAMPLES

Example 1

Preparation of 3-(2-Benzyloxy-3,6-dichloro-phenyl)-4-hydroxy-1-prop-2-ynyl-1,8-naphthyridin-2-one

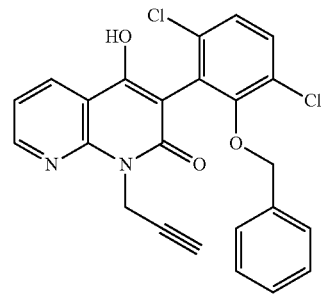

1.1 2-Allyl-3,6-dichloro-phenol

A mixture of 2-allyloxy-1,4-dichloro-benzene (1.0 g, 4.9 mmol, 1.0 eq.) and DMF (0.1 mL) was heated at an external temperature of 220° C. for 1 hour. The mixture was allowed to cool to room temperature and was concentrated in vacuo to provide 2-allyl-3,6-dichloro-phenol as a brown oil (0.99 g, 99%).

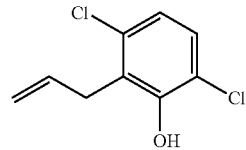

$^1$H NMR (400 MHz, CDCl$_3$): $\delta_H$: 7.18-7.08 (1H, m) 6.95-6.85 (1H, m) 6.02-5.84 (1H, m) 5.71 (1H, s) 5.14-4.99 (2H, m) 3.59 (2H, dt).

1.2 2-Allyl-3-benzyloxy-1,4-dichloro-benzene

Benzyl bromide (3.2 mL, 27 mmol, 1.1 eq.) was added to a suspension of 2-allyl-3,6-dichloro-phenol (5.0 g, 25 mmol, 1.0 eq.) and potassium carbonate (3.7 g, 27 mmol, 1.1 eq.) in acetone (49 mL) and the mixture was heated at reflux for 6 hours. The mixture was allowed to cool to room temperature and was filtered. The filtrate was concentrated in vacuo and the crude product was purified by flash column chromatography to provide 2-allyl-3-benzyloxy-1,4-dichloro-benzene (4.031 g, 56%) as a colorless oil.

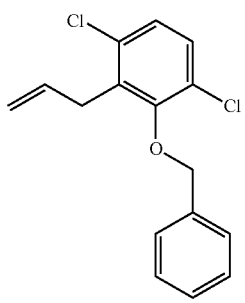 [SMILES: C=CCc1c(Cl)ccc(Cl)c1OCc1ccccc1]

¹H NMR (400 MHz, CDCl₃): δ$_H$: 7.54-7.49 (2H, m), 7.45-7.35 (3H, m), 7.27-7.24 (1H, m), 7.15 (1H, d), 6.01-5.90 (1H, m), 5.10-4.97 (4H, m), 3.59 (2H, dt).

1.3 2-(2-Benzyloxy-3,6-dichloro-phenyl)acetic acid

A solution of 2-allyl-3-benzyloxy-1,4-dichloro-benzene (38.1 g, 130 mmol, 1.00 eq.) in dichloromethane (650 mL) in a 3-necked flask was cooled to −78° C. One side neck was connected to a Dreshel bottle containing an aqueous solution of KI (100 mL, 15% w/w). Ozone was bubbled through the solution until 2-allyl-3-benzyloxy-1,4-dichloro-benzene had been fully consumed (4 hours). Air was bubbled through the solution for 10 minutes to remove excess ozone. The bubbling of gas through the solution was stopped and dimethyl sulfide (95.4 mL, 1300 mmol, 10.0 eq.) was added. The mixture was allowed to warm to room temperature and was stirred for 12 hours. The mixture was washed with brine (2×200 mL) and the organic extracts were passed through a hydrophobic frit. The mixture was concentrated in vacuo to provide a yellow oil (43 g). The residue was dissolved in a mixture of in tert-butanol (260 mL) and water (130 mL) then cooled to 0° C. 2-Methylpropene (135 mL, 1300 mmol, 10.0 eq.), sodium dihydrogen phosphate (62.4 g, 520 mmol, 4.00 eq.) and sodium chlorite (44.1 g, 390 mmol, 3.00 eq.) were added. The mixture was stirred for 2 hours then diluted with brine (300 mL) and an aqueous solution of HCl (300 mL, 2.0 M). The mixture was extracted with EtOAc (3×200 mL). The combined organic extracts were washed with a saturated aqueous solution of sodium metabisulfite (200 mL) then passed through a hydrophobic frit and concentrated in vacuo to provide a pale yellow solid (41.4 g). The residue was suspended in H₂O (200 mL) and an aqueous solution of NaOH (30 mL, 2.0 M) was added resulting in a clear solution. The mixture was washed with Et₂O (100 mL) and the aqueous layer was acidified by addition of concentrated HCl (20 mL) resulting in the formation of a precipitate. The mixture was filtered and the filtrand was dried in vacuo to provide 2-(2-benzyloxy-3,6-dichloro-phenyl)acetic acid (29.2 g, 72%) as a white solid.

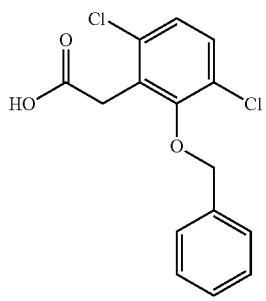 [SMILES: O=C(O)Cc1c(Cl)ccc(Cl)c1OCc1ccccc1]

¹H NMR (400 MHz, CDCl₃): δ$_H$: 7.48-7.44 (2H, m), 7.42-7.31 (4H, m), 7.17 (1H, d), 5.04 (2H, s), 3.85 (2H, s).

1.4 Ethyl 2-{[2-(2-benzyloxy-3,6-dichloro-phenyl) acetyl]amino}pyridine-3-carbo-xylate Oxalyl chloride (4.2 mL, 48.2 mmol, 2.00 eq.) was added to a suspension of 2-(2-benzyloxy-3,6-dichloro-phenyl)acetic acid (7.50 g, 24.1 mmol, 1.00 eq.) in a mixture of dichloromethane (90 mL) and DMF (0.1 mL) dropwise over a period of 10 minutes. The mixture was stirred for 1 hour until the effervescence ceased. The mixture was concentrated in vacuo. The residue was dissolved in CH₂Cl₂ (50 mL) and a solution of ethyl 2-aminopyridine-3-carboxylate (4.00 g, 24.1 mmol, 1.00 eq.) and pyridine (2.29 g, 3.35 mL, 28.9 mmol, 1.20 eq.) in CH₂Cl₂ (30 mL) was added via syringe at 0° C. The reaction mixture was stirred at room temperature for 16 hours. The mixture was poured into H₂O (50 mL) and the mixture was separated. The organic extracts were passed through a hydrophobic frit and concentrated in vacuo. The crude material was dissolved in CH₂Cl₂ (50 mL) and isohexane (150 mL) was added resulting in the formation of a precipitate. The mixture was filtered and the filtrand was dried in vacuo to provide ethyl 2-{[2-(2-benzyloxy-3, 6-dichloro-phenyl)acetyl]amino}pyridine-3-carboxylate (6.492 g, 58%) as a beige solid.

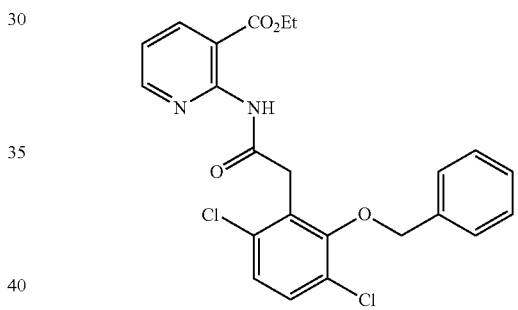

¹H NMR (500 MHz, CDCl₃): δ$_H$: 10.87 (1H, s), 8.57 (1H, dd), 8.31 (1H, dd), 7.49-7.45 (2H, m), 7.35-7.27 (4H, m), 7.18 (1H, d), 7.06 (1H, dd), 5.09 (2H, s), 4.37 (2H, q), 4.24 (2H, s), 1.40 (3H, t).

1.5 3-(2-Benzyloxy-3,6-dichloro-phenyl)-4-hydroxy-1H-1,8-naphthyridin-2-one

A solution of LiHMDS (1.0 M in THF, 39 mL, 39.0 mmol, 2.80 eq.) was added to a solution of ethyl 2-{[2-(2-benzyloxy-3,6-dichloro-phenyl)acetyl]amino}pyridine-3-carboxylate (6.40 g, 13.9 mmol, 1.00 eq.) in tetrahydrofuran (139 mL) dropwise over 30 minutes resulting in a dark brown solution. The reaction mixture was stirred at room temperature for 12 hours. The reaction mixture was quenched by addition of H₂O (20 mL). The tetrahydrofuran was removed in vacuo. H₂O (100 mL) and charcoal (1.0 g) were added to the residue and the mixture was filtered through celite. The filtrate was acidified by addition of concentrated HCl (10 mL) resulting in the formation of a precipitate. The mixture was filtered and the filtrand was dried in vacuo to provide 3-(2-benzyloxy-3,6-dichloro-phenyl)-4-hydroxy-1H-1,8-naphthyridin-2-one (5.524 g, 95%) as a beige solid.

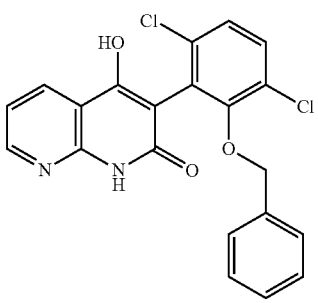 [SMILES: O=c1[nH]c2ncccc2c(O)c1-c1c(Cl)ccc(Cl)c1OCc1ccccc1]

¹H NMR (400 MHz, DMSO-d₆): δ_H: 11.91 (1H, s), 10.93 (1H, br. s), 8.56 (1H, dd), 8.30 (1H, dd), 7.59 (1H, d), 7.41 (1H, d), 7.26 (1H, dd), 7.18-7.09 (5H, m), 4.84 (1H, d), 4.80 (1H, d).

1.6 [3-(2-Benzyloxy-3,6-dichloro-phenyl)-2-oxo-1H-1,8-naphthyridin-4-yl]2-methylpropanoate 2-Methylpropanoyl chloride (1.99 mL, 18.6 mmol, 1.40 eq.) was added to a suspension of 3-(2-benzyloxy-3,6-dichloro-phenyl)-4-hydroxy-1H-1,8-naphthyridin-2-one (5.48 g, 13.3 mmol, 1.00 eq.), pyridine (1.61 mL, 19.9 mmol, 1.50 eq.) and 4-dimethylaminopyridine (0.162 g, 1.33 mmol, 0.100 eq.) in dichloromethane (54 mL) and the reaction mixture was stirred for 2 hours. The mixture was diluted with CH₂Cl₂ (30 mL) and was washed with an aqueous solution of HCl (20 mL, 2.0 M) then a saturated aqueous solution of NaHCO₃ (20 mL). The combined organic extracts were passed through a hydrophobic frit and concentrated in vacuo. The residue was dissolved in CH₂Cl₂ (20 mL) and isohexane (100 mL) was added slowly resulting in the formation of a precipitate. The mixture was filtered to provide [3-(2-benzyloxy-3,6-dichloro-phenyl)-2-oxo-1H-1,8-naphthyridin-4-yl] 2-methylpropanoate (5.358 g, 84%) as a beige solid.

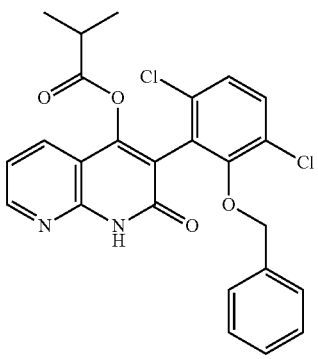 [SMILES: CC(C)C(=O)Oc1c(-c2c(Cl)ccc(Cl)c2OCc2ccccc2)c(=O)[nH]c2ncccc12]

¹H NMR (400 MHz, CDCl₃): δ_H: 12.07 (1H, br. s), 8.81 (1H, dd), 7.80 (1H, dd), 7.43 (1H, d), 7.27-7.22 (2H, m), 7.18 (2H, dd), 7.08-7.03 (3H, m), 5.08 (1H, d), 4.82 (1H, d), 2.70 (1H, spt), 1.09 (3H, d), 1.06 (3H, d).

1.7 [3-(2-Benzyloxy-3,6-dichloro-phenyl)-2-oxo-1-prop-2-ynyl-1,8-naph-thyridin-4-yl]2-methylpropanoate A solution of [3-(2-benzyloxy-3,6-dichloro-phenyl)-2-oxo-1H-1,8-naphthyridin-4-yl] 2-methylpropanoate (2.64 g, 5.46 mmol, 1.00 eq.) in DMF (5.0 mL) was added to a suspension of sodium hydride (0.240 g, 6.01 mmol, 1.10 eq.) in DMF (27 mL) at 0° C. The mixture was stirred for 1 hour. A solution of propargyl bromide (80% in toluene, 1.03 mL, 9.29 mmol, 1.70 eq.) was added and the reaction mixture was allowed to warm to room temperature and was stirred at room temperature for 3 hours. The mixture was diluted with EtOAc (50 mL) and the mixture was washed with H₂O (20 mL) and brine (20 mL). The organic extracts were dried over MgSO₄, filtered and concentrated in vacuo. The crude product was purified by flash column chromatography to provide [3-(2-benzyloxy-3,6-dichloro-phenyl)-2-oxo-1-prop-2-ynyl-1,8-naphthyridin-4-yl] 2-methylpropanoate (2.039 g, 72%) as an orange solid.

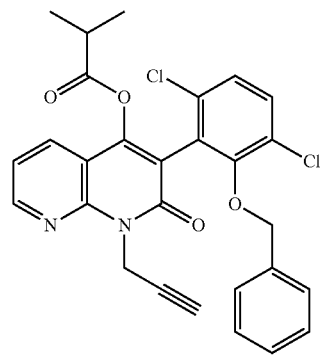 [SMILES: C#CCn1c(=O)c(-c2c(Cl)ccc(Cl)c2OCc2ccccc2)c(OC(=O)C(C)C)c2cccnc21]

¹H NMR (400 MHz, CDCl₃) δ_H: 8.71 (1H, dd), 7.76 (1H, dd), 7.40 (1H, d), 7.26-7.21 (2H, m), 7.17-7.03 (5H, m), 5.23 (2H, dd), 5.06 (1H, d), 4.77 (1H, d), 2.67 (1H, spt), 2.09 (1H, t), 1.06 (3H, d), 1.03 (3H, d).

1.8 Preparation of 3-(2-Benzyloxy-3,6-dichloro-phenyl)-4-hydroxy-1-prop-2-ynyl-1,8-naphthyridin-2-one A solution of freshly ground potassium hydroxide (0.504 g, 7.63 mmol, 2.00 eq.) in water (15 mL) was added to a solution of [3-(2-benzyloxy-3,6-dichloro-phenyl)-2-oxo-1-prop-2-ynyl-1,8-naphthyridin-4-yl] 2-methylpropanoate (1.99 g, 3.82 mmol, 1.00 eq.) in tetrahydrofuran (38 mL). The mixture was stirred at room temperature for 24 hours. The mixture was concentrated in vacuo. The residue was suspended in H₂O (20 mL) and the mixture was acidified by addition of an aqueous solution of HCl (5.0 mL, 2.0 M) resulting in the formation of a precipitate. The mixture was filtered and the filtrand was dissolved in CH₂Cl₂ (20 mL). The mixture was passed through a hydrophobic frit and concentrated in vacuo to provide a green foam. The mixture was dissolved in CH₂Cl₂ (5.0 mL) and isohexane (20 mL) was added resulting in the formation of a precipitate. The mixture was filtered and the filtrand was dried in vacuo to provide 3-(2-benzyloxy-3,6-dichloro-phenyl)-4-hydroxy-1-prop-2-ynyl-1,8-naphthyridin-2-one (1.155 g, 67%) as an orange solid.

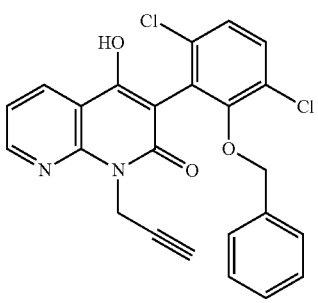 [SMILES: C#CCn1c(=O)c(-c2c(Cl)ccc(Cl)c2OCc2ccccc2)c(O)c2cccnc21]

$^1$H NMR (400 MHz, CDCl$_3$) δ$_H$: 8.71 (1H, dd), 8.24 (1H, dd), 7.44 (1H, d), 7.29 (1H, d), 7.23 (1H, dd), 7.16-7.03 (5H, m), 6.39 (1H, br. s.), 5.26 (2H, d), 5.09 (1H, d), 4.77 (1H, d), 2.11 (1H, t).

Example 2

Intermediate Production According to Reaction Scheme 6, Amination of Pyridine Compound: Preparation of Ethyl 2-amino-4-methoxy-pyridine-3-carboxylate Benzophenone imine (4.3 mL, 26 mmol, 1.1 eq.) was added to a solution of ethyl 2-chloro-4-methoxy-pyridine-3-carboxylate (5.0 g, 23 mmol, 1.0 eq.), Pd$_2$(dba)$_3$ (0.43 g, 0.46 mmol, 0.020 eq.), BINAP (0.74 g, 1.2 mmol, 0.050 eq.) and sodium tert-butoxide (2.8 g, 28 mmol, 1.2 eq.) in toluene (75 mL). The mixture was heated at 100° C. for 30 minutes. The mixture was allowed to cool to room temperature and was diluted with EtOAc (200 mL). The mixture was washed with H$_2$O (2×50 mL) and brine (50 mL) and organic extracts were passed through a hydrophobic frit and concentrated in vacuo to provide a brown oil. The residue was dissolved in THF (70 mL) and an aqueous solution of HCl (6.0 M, 10 mL, 60 mmol, 2.6 eq.) was added. The mixture was stirred at room temperature for 16 hours. The mixture was diluted with CH$_2$Cl$_2$ (200 mL) and a saturated aqueous solution of NaHCO$_3$ (100 mL) was added cautiously. The mixture was separated and the aqueous layer was extracted with CH$_2$Cl$_2$ (100 mL). The combined organic extracts were passed through a hydrophobic frit and concentrated in vacuo. The crude product was purified by flash column chromatography (0-100% EtOAc in isohexane) to provide ethyl 2-amino-4-methoxy-pyridine-3-carboxylate (3.679 g, 81%) as an orange solid.

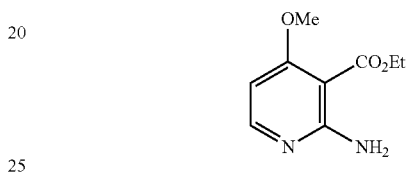

$^1$H NMR (400 MHz, CDCl$_3$): δ$_H$: 8.01 (1H, d), 6.23 (1H, d), 6.10 (2H, br. s), 4.35 (2H, q), 3.86 (3H, s), 1.37 (3H, t).

The compounds in the following tables were made in an analogous manner using the general methodology described hereinbefore, in particular with reference to Examples 1 and 2 above.

TABLE 1

Describes 8 compounds of formula (I-1) below, wherein A$_1$ and Z$^1$ to Z$^5$ are as specified.

(I-1)

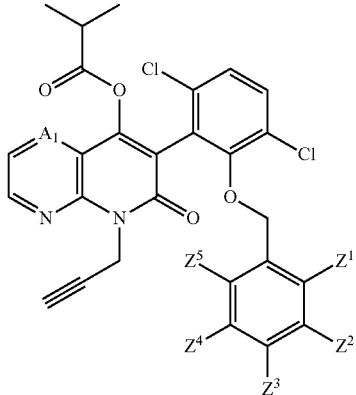

| Compound | A$_1$ | Z$^1$ | Z$^2$ | Z$^3$ | Z$^4$ | Z$^5$ | NMR data |
|---|---|---|---|---|---|---|---|
| 1.001 | CH | H | H | H | H | H | (CDCl$_3$) 8.71 (1H, dd), 7.76 (1H, dd), 7.40 (1H, d), 7.26-7.21 (2H, m), 7.17-7.03 (5H, m), 5.23 (2H, dd), 5.06 (1H, d), 4.77 (1H, d), 2.67 (1H, spt), 2.09 (1H, t), 1.06 (3H, d), 1.03 (3H, d). |
| 1.002 | CH | H | H | OMe | H | H | (CDCl$_3$) 8.69 (1H, dd), 7.75 (1H, dd), 7.37 (1H, d), 7.24-7.21 (1H, m), 7.21-7.17 (1H, m), 7.03 (2H, d), 6.55 (2H, d), 5.24 (2H, d), 4.97-4.64 (2H, m), 3.65 (3H, s), 2.64 (1H, spt), 2.11 (1H, t), 1.04-0.99 (6H, m). |
| 1.003 | CH | H | H | Cl | H | H | (CDCl$_3$) 8.74 (1H, dd), 7.76 (1H, dd), 7.41 (1H, d), 7.26-7.22 (1H, m), 7.29-7.22 (1H, m), 7.13-7.01 (4H, m), 5.27 (2H, dd), 5.03 (1H, d), 4.77 (1H, d), 2.68 (1H, spt), 2.11 (1H, ), 1.08-1.05 (6H, m). |

TABLE 1-continued

Describes 8 compounds of formula (I-1) below, wherein $A_1$ and $Z^1$ to $Z^5$ are as specified.

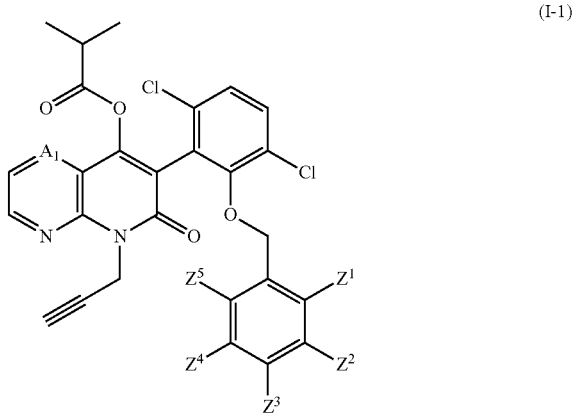

(I-1)

| Compound | $A_1$ | $Z^1$ | $Z^2$ | $Z^3$ | $Z^4$ | $Z^5$ | NMR data |
|---|---|---|---|---|---|---|---|
| 1.004 | CH | H | H | Me | H | H | (CDCl$_3$) 8.72 (1H, dd), 7.76 (1H, dd), 7.40 (1H, d), 7.24-7.21 (1H, m), 7.26-7.21 (1H, m), 7.03 (2H, d 7.9), 6.86 (2H, d), 5.26 (2H, d), 5.02 (1H, d), 4.71 (1H, d), 2.67 (1H, spt), 2.19 (3H, s), 2.11 (1H, t), 1.08-1.03 (6H, m). |
| 1.005 | CH | H | Cl | Cl | H | H | (CDCl$_3$) 8.71 (1H, dd), 8.31 (1H, dd), 7.46 (1H, d), 7.33-7.27 (2H, m), 7.26-7.22 (1H, m), 7.17-7.11 (1H, m), 7.02-6.96 (1H, m), 5.17 (1H, d), 4.74 (1H, d), 4.48-4.34 (2H, m), 2.70 (1H, spt), 2.50 (1H, t), 1.09-1.07 (6H, m). |
| 1.006 | CH | H | H | CF$_3$ | H | H | (CDCl$_3$) 8.72 (1H, dd), 7.76 (1H, dd), 7.43 (1H, d), 7.37-7.33 (1H, m), 7.35-7.28 (4H, m), 7.26-7.21 (1H, m), 5.24 (2H, d), 5.15 (1H, d), 4.89 (1H, d), 2.69 (1H, spt), 2.09-2.07 (1H, m), 1.08-1.06 (6H, m). |
| 1.007 | C—OMe | H | H | H | H | H | (CDCl$_3$) 8.54 (1H, d), 7.39 (1H, d), 7.24-7.10 (6H, m), 6.70 (1H, d), 5.33-4.76 (4H, m), 3.91 (3H, s), 2.59 (1H, spt), 2.07 (1H, br. s.), 1.04-0.93 (6H, m). |
| 1.008 | N | H | H | H | H | H | (CDCl$_3$) 8.61 (1H, d), 8.51 (1H, d), 7.44 (1H, d), 7.26 (1H, d), 7.18 (2H, dd), 7.11-7.03 (3H, m), 5.13 (2H, dd), 5.03 (1H, d), 4.90 (1H, d), 2.79 (1H, spt), 2.13 (1H, t), 1.17 (3H, d), 1.14 (3H, d). |

TABLE 2

Describes 8 compounds of formula (I-2) below, wherein $A_1$ and $Z^1$ to $Z^5$ are as specified.

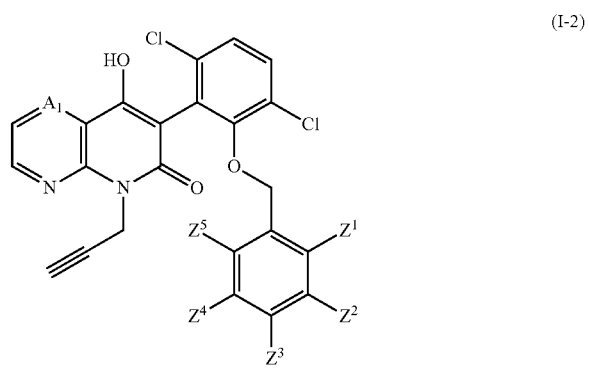

(I-2)

| Compound | $A_1$ | $Z^1$ | $Z^2$ | $Z^3$ | $Z^4$ | $Z^5$ | NMR data |
|---|---|---|---|---|---|---|---|
| 2.001 | CH | H | H | H | H | H | (CDCl$_3$) 8.71 (1H, dd), 8.24 (1H, dd), 7.44 (1H, d), 7.29 (1H, d), 7.23 (1H, dd), 7.16-7.03 (5H, m), 6.39 (1H, br. s.), 5.26 (2H, d), 5.09 (1H, d), 4.77 (1H, d), 2.11 (1H, t). |

TABLE 2-continued

Describes 8 compounds of formula (I-2) below, wherein $A_1$ and $Z^1$ to $Z^5$ are as specified.

(I-2)

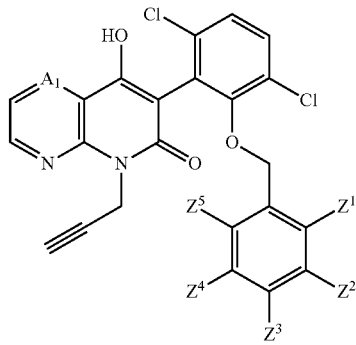

| Compound | $A_1$ | $Z^1$ | $Z^2$ | $Z^3$ | $Z^4$ | $Z^5$ | NMR data |
|---|---|---|---|---|---|---|---|
| 2.002 | CH | H | H | OMe | H | H | (CDCl$_3$) 8.71 (1H, dd), 8.23 (1H, dd), 7.45 (1H, d), 7.30 (1H, d), 7.23 (1H, dd), 7.04 (2H, d), 6.57 (2H, d), 5.30 (2H, d), 5.06-4.68 (2H, m), 3.66 (3H, s), 2.13 (1H, t). |
| 2.003 | CH | H | H | Cl | H | H | (CDCl$_3$) 8.76-8.72 (1H, m), 8.25-8.20 (1H, m), 7.49 (1H, d), 7.34 (1H, d), 7.26-7.23 (1H, m), 7.10-7.00 (4H, m), 5.30 (2H, d), 5.07 (1H, s), 4.76 (1H, d), 2.13 (1H, s). |
| 2.004 | CH | H | H | Me | H | H | (CDCl$_3$) 8.72 (1H, dd), 8.22 (1H, dd), 7.48 (1H, d), 7.32 (1H, d), 7.23 (1H, dd), 7.02 (2H, d), 6.87 (2H, d), 5.96 (1H, br. s.), 5.30 (2H, t), 5.08 (1H, d), 4.72 (1H, d), 2.18 (3H, s), 2.14 (1H, t). |
| 2.005 | CH | H | Cl | Cl | H | H | (CDCl$_3$) 8.73 (1H, dd), 8.26 (1H, dd), 7.50 (1H, d), 7.35 (1H, d), 7.30-7.24 (1H, m), 7.22 (1H, d), 7.13 (1H, d), 6.99 (1H, d), 5.28 (2H, d), 5.07 (1H, d), 4.76 (1H, d), 2.12 (1H, t). |
| 2.006 | CH | H | H | CF$_3$ | H | H | (CDCl$_3$) 8.70 (1H, dd), 8.21 (1H, dd), 7.47 (1H, d), 7.34-7.25 (5H, m), 7.22 (1H, dd), 5.25 (2H, d), 5.16 (1H, d), 4.86 (1H, d), 2.11 (1H, t). |
| 2.007 | C—OMe | H | H | H | H | H |  |
| 2.008 | N | H | H | H | H | H | (CDCl$_3$) 8.69 (1H, d), 8.41 (1H, d), 7.89 (1H, br. s.), 7.45 (1H, d), 7.30-7.26 (1H, m), 7.22-7.12 (2H, m), 7.00 (3H, d), 5.20 (1H, dd), 5.15 (1H, dd), 4.99 (2H, s), 2.17 (1H, t). |

TABLE 3

Describes 8 compounds of formula (I-3) below, wherein $A_1$ and $Z^1$ to $Z^5$ are as specified.

(I-3)

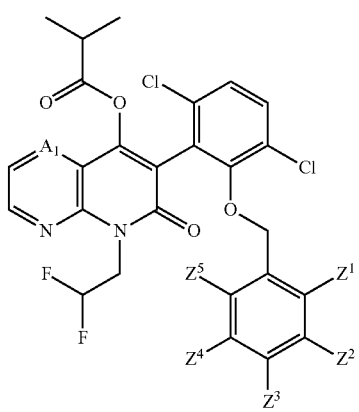

| Compound | $A_1$ | $Z^1$ | $Z^2$ | $Z^3$ | $Z^4$ | $Z^5$ | NMR data |
|---|---|---|---|---|---|---|---|
| 3.001 | CH | H | H | H | H | H | (CDCl$_3$) 8.67 (1H, dd), 7.81 (1H, dd), 7.43 (1H, d), 7.30-7.24 (2H, m), 7.18-7.06 (5H, m), 6.19 (1H, tt), 5.08 (1H, d), 5.02-4.81 (2H, m), 4.79 (1H, d), 2.71 (1H, spt), 1.10 (3H, d), 1.07 (3H, d). |

TABLE 3-continued

Describes 8 compounds of formula (I-3) below, wherein $A_1$ and $Z^1$ to $Z^5$ are as specified.

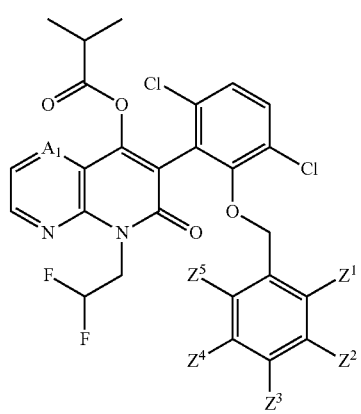

(I-3)

| Compound | $A_1$ | $Z^1$ | $Z^2$ | $Z^3$ | $Z^4$ | $Z^5$ | NMR data |
|---|---|---|---|---|---|---|---|
| 3.002 | CH | H | H | OMe | H | H | (CDCl$_3$) 8.67 (1H, dd), 7.81 (1H, dd), 7.41 (1H, d), 7.29-7.25 (1H, m), 7.23 (1H, d), 7.05 (2H, d), 6.60 (2H, d), 6.38-6.05 (1H, m), 4.95 (2H, m), 4.99-4.69 (2H, m), 3.70 (3H, s), 2.69 (1H, spt), 1.09-1.04 (6H, m). |
| 3.003 | CH | H | H | Cl | H | H | (CDCl$_3$) 8.68 (1H, dd), 7.79 (1H, dd), 7.42 (1H, d), 7.31-7.27 (1H, m), 7.25 (1H, d), 7.11-7.03 (4H, m), 6.37-6.04 (1H, m), 5.02 (1H, d), 4.99-4.81 (2H, m), 4.75 (1H, d), 2.69 (1H, spt), 1.09-1.06 (6H, m). |
| 3.004 | CH | H | H | Me | H | H | (CDCl$_3$) 8.66 (1H, dd), 7.79 (1H, dd), 7.41 (1H, d), 7.28-7.25 (1H, m), 7.25-7.22 (1H, m), 7.01 (2H, d), 6.87 (2H, d), 6.35-6.02 (1H, m), 5.02 (1H, d), 4.98-4.83 (2H, m), 4.71 (1H, d), 2.69 (1H, spt), 2.21 (3H, s), 1.09-1.04 (6H, m). |
| 3.005 | CH | H | Cl | Cl | H | H | (CDCl$_3$) 8.68 (1H, dd), 7.81 (1H, dd), 7.43 (1H, d), 7.30-7.25 (3H, m), 7.26 (1H, d), 7.17 (1H, d), 6.97 (1H, dd), 6.36-6.03 (1H, m), 5.04 (1H, d), 5.02-4.78 (2H, m), 4.75 (1H, d), 2.71 (1H, spt), 1.10-1.07 (6H, m). |
| 3.006 | CH | H | H | CF$_3$ | H | H | (CDCl$_3$) 8.66 (1H, dd), 7.79 (1H, dd), 7.44 (1H, d), 7.38-7.34 (2H, m), 7.29-7.26 (2H, m), 7.28-7.25 (1H, m), 7.30-7.24 (1H, m), 6.33-5.99 (1H, m), 5.14 (1H, d), 4.86 (1H, d), 5.01-4.75 (2H, m), 2.71 (1H, spt), 1.10-1.07 (6H, m). |
| 3.007 | C—OMe | H | H | H | H | H | (CDCl$_3$) 8.48 (1H, d), 7.39 (1H, d), 7.25-7.11 (6H, m), 6.71 (1H, d), 6.33-5.97 (1H, m), 5.06-4.77 (4H, m), 3.92 (3H, s), 2.61 (1H, spt), 1.05-0.94 (6H, m). |
| 3.008 | N | H | H | H | H | H | (CDCl$_3$) 8.57 (1H, d), 8.53 (1H, d), 7.48-7.42 (1H, m), 7.26 (1H, d), 7.19-7.04 (5H, m), 6.09 (1H, tt), 5.02 (1H, d), 4.90 (1H, d), 4.87-4.67 (2H, m), 2.81 (1H, spt), 1.20-1.13 (6H, m). |

TABLE 4

Describes 8 compounds of formula (I-4) below, wherein $A_1$ and $Z^1$ to $Z^5$ are as specified.

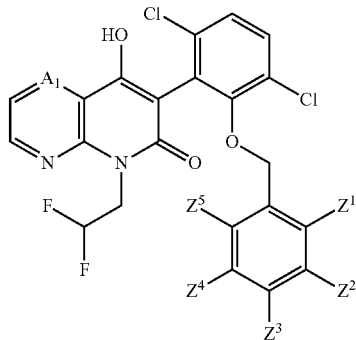

(I-4)

| Compound | $A_1$ | $Z^1$ | $Z^2$ | $Z^3$ | $Z^4$ | $Z^5$ | NMR data |
|---|---|---|---|---|---|---|---|
| 4.001 | CH | H | H | H | H | H | (CDCl$_3$) 8.64 (1H, dd 4.6), 8.26 (1H, dd), 7.43 (1H, d), 7.28 (1H, d), 7.25 (1H, dd), 7.14-7.03 (5H, m), 6.22 (1H, tt), 5.08 (1H, d), 4.98-4.82 (2H, m), 4.74 (1H, d). |
| 4.002 | CH | H | H | OMe | H | H | (CDCl$_3$) 8.64 (1H, dd), 8.28 (1H, dd), 7.37 (1H, d), 7.26-7.23 (1H, m), 7.23-7.20 (1H, m), 6.99 (2H, d), 6.55 (2H, d), 6.39-6.06 (1H, m), 4.96 (1H, d), 4.94-4.85 (2H, m), 4.68 (1H, d), 3.66 (3H, s). |
| 4.003 | CH | H | H | Cl | H | H | (CDCl$_3$) 8.67 (1H, dd), 8.25 (1H, dd), 7.50 (1H, d), 7.35 (1H, d), 7.30-7.25 (1H, m), 7.04 (4H, d), 6.42-6.10 (1H, m), 5.07 (1H, d 11.4), 5.01-4.83 (2H, m), 4.74 (1H, d). |
| 4.004 | CH | H | H | Me | H | H | (CDCl$_3$) 8.65 (1H, dd), 8.25 (1H, dd), 7.49 (1H, d), 7.33 (1H, d), 7.26-7.20 (1H, m), 6.99 (2H, d), 6.86 (2H, d), 6.43-6.08 (1H, m), 6.05-5.91 (1H, m), 5.08 (1H, d), 5.04-4.83 (2H, m), 4.71 (1H, d), 2.19 (3H, s). |
| 4.005 | CH | H | Cl | Cl | H | H | (DMSO-d$_6$) 8.70-8.64 (1H, m), 8.31 (1H, d), 7.61 (1H, d), 7.42 (1H, d), 7.39-7.34 (1H, m), 7.29 (1H, d), 7.19 (1H, d), 7.08 (1H, s), 6.45-6.09 (1H, m), 4.85 (2H, d), 4.80-4.69 (2H, m). |
| 4.006 | CH | H | H | CF$_3$ | H | H | (DMSO-d$_6$) 8.67-8.60 (1H, m), 8.32-8.25 (1H, m), 7.65-7.59 (1H, m), 7.46-7.40 (1H, m), 7.35-7.30 (1H, m), 7.39-7.24 (4H, m), 6.43-6.07 (1H, m), 4.99-4.89 (2H, m), 4.78-4.66 (2H, m). |
| 4.007 | C—OMe | H | H | H | H | H | (CDCl$_3$) 9.08 (1H, s), 8.51 (1H, d), 7.40 (1H, d), 7.29-7.23 (1H, m), 7.21-7.06 (5H, m), 6.74 (1H, d), 6.22 (1H, tt), 5.01-4.86 (4H, m), 4.09 (3H, s). |
| 4.008 | N | H | H | H | H | H | (CDCl$_3$) 8.65 (1H, d), 8.44 (1H, d), 7.99 (1H, br. s), 7.46 (1H, d), 7.29 (1H, d), 7.18-7.08 (2H, m), 7.01 (3H, d), 6.17 (1H, tt), 4.98 (2H, s), 4.90-4.71 (2H, m). |

TABLE 5

Describes 3 compounds of formula (I-5) below, wherein $A_1$, $R^6$ and $Z^1$ to $Z^5$ are as specified.

(I-5)

| Compound | $A_1$ | $R^6$ | $Z^1$ | $Z^2$ | $Z^3$ | $Z^4$ | $Z^5$ | NMR data |
|---|---|---|---|---|---|---|---|---|
| 5.001 | CH | $^i$Pr | H | H | H | H | H | (CDCl$_3$) 8.72 (1H, dd) 7.78 (1H, dd) 7.44 (1H, dd) 7.24 (1H, dd) 7.17 (2H, m) 7.09 (3H, m) 6.84 (1H, m) 5.24 (2H, m) 5.06 (1H, d) 4.82 (1H, d) 2.70 (1H, spt) 2.13 (1H, t) 1.11 (3H, d) 1.09 (3H, d). |
| 5.002 | C—OMe | Me | H | H | H | H | H | (CDCl$_3$) 8.55 (1H, d) 7.43 (1H, dd) 7.17 (5H, m) 6.93 (1H, t) 6.71 (1H, d) 5.22 (2H, m) 4.87 (2H, m) 3.95 (3H, s) 2.11 (4H, m). |
| 5.003 | N | $^i$Pr | H | H | H | H | H | (CDCl$_3$) 8.62 (1H, d) 8.51 (1H, d) 7.47 (1H, dd) 7.20 (2H, dd) 7.08 (3H, m) 6.95 (1H, t) 5.13 (2H, qd) 4.98 (2H, m) 2.81 (1H, spt) 2.15 (1H, t) 1.19 (6H, m). |

TABLE 6

Describes 3 compounds of formula (I-6) below, wherein $A_1$ and $Z^1$ to $Z^5$ are as specified.

(I-6)

| Compound | $A_1$ | $Z^1$ | $Z^2$ | $Z^3$ | $Z^4$ | $Z^5$ | NMR data |
|---|---|---|---|---|---|---|---|
| 6.001 | CH | H | H | H | H | H | (CDCl$_3$) 8.71 (1H, dd) 8.24 (1H, dd) 7.49 (1H, dd) 7.22 (1H, dd) 7.15 (2H, m) 7.09 (3H, m) 7.01 (1H, t) 6.77 (1H, s) 6.78 (1H, br. s.) 5.29 (2H, m) 5.18 (1H, d) 4.74 (1H, m) 2.15 (1H, t). |
| 6.002 | C—OMe | H | H | H | H | H | (CDCl$_3$) 9.04 (1H, s) 8.57 (1H, d) 7.42 (1H, dd) 7.23 (2H, d) 7.08 (3H, m) 6.94 (1H, t) 6.72 (1H, d) 5.26 (2H, m) 4.98 (2H, m) 4.08 (3H, s) 2.12 (1H, t). |
| 6.003 | N | H | H | H | H | H | (CDCl$_3$) 8.69 (1H, d) 8.41 (1H, d) 7.93 (1H, s) 7.93 (1H, br. s.) 7.47 (1H, dd) 7.18 (2H, d) 6.99 (4H, m) 5.18 (2H, m) 5.02 (2H, m) 2.18 (1H, s). |

TABLE 7

Describes 3 compounds of formula (I-7) below, wherein $A_1$, $R^6$ and $Z^1$ to $Z^5$ are as specified.

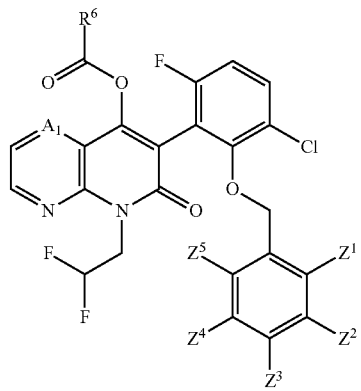

(I-7)

| Compound | $A_1$ | $R^6$ | $Z^1$ | $Z^2$ | $Z^3$ | $Z^4$ | $Z^5$ | NMR data |
|---|---|---|---|---|---|---|---|---|
| 7.001 | CH | $^i$Pr | H | H | H | H | H | (CDCl$_3$) 8.66 (1H, dd) 7.81 (1H, dd) 7.45 (1H, dd) 7.26 (1H, dd) 7.11 (5H, m) 6.95 (1H, t) 6.13 (1H, m) 5.05 (1H, d) 4.88 (3H, m) 2.72 (1H, spt) 1.11 (6H, m). |
| 7.002 | C—OMe | Me | H | H | H | H | H | (CDCl$_3$) 8.48 (1H, d) 7.44 (1H, dd) 7.18 (5H, m) 6.84 (1H, m) 6.72 (1H, d) 5.10 (1H, m) 4.90 (4H, m) 3.96 (3H, s) 2.12 (3H, s). |
| 7.003 | N | $^i$Pr | H | H | H | H | H | (CDCl$_3$) 8.57 (1H, d) 8.53 (1H, d 2.2) 7.49 (1H, dd) 7.12 (5H, m) 6.96 (1H, t) 5.03 (1H, m) 4.97 (2H, m) 4.78 (2H, m) 2.82 (1H, spt) 1.19 (6H, m). |

TABLE 8

Describes 3 compounds of formula (I-8) below, wherein $A_1$ and $Z^1$ to $Z^5$ are as specified.

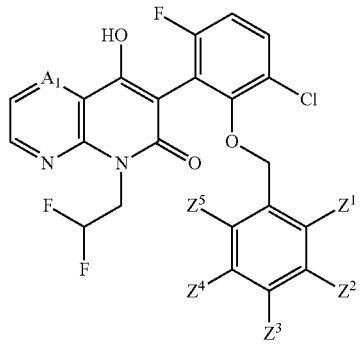

(I-8)

| Compound | $A_1$ | $Z^1$ | $Z^2$ | $Z^3$ | $Z^4$ | $Z^5$ | NMR data |
|---|---|---|---|---|---|---|---|
| 8.001 | CH | H | H | H | H | H | (CDCl$_3$) 8.65 (1H, dd) 8.26 (1H, dd) 7.50 (1H, m) 7.24 (1H, dd) 7.06 (6H, m) 6.81 (1H, br. s.) 6.26 (1H, m) 5.19 (1H, d) 4.95 (2H, m) 4.74 (1H, d). |
| 8.002 | C—OMe | H | H | H | H | H | (CDCl$_3$) 9.11 (1H, s) 8.50 (1H, d) 7.42 (1H, dd) 7.19 (2H, m) 7.09 (3H, m) 6.94 (1H, t) 6.74 (1H, d) 6.22 (1H, m) 4.93 (4H, m) 4.09 (3H, s). |
| 8.003 | N | H | H | H | H | H | (CDCl$_3$) 8.65 (1H, d) 8.44 (1H, d) 8.02 (1H, br. s.) 7.48 (1H, dd) 7.13 (2H, dd) 6.99 (4H, m) 5.12 (1H, m) 5.01 (2H, m) 4.80 (2H, m). |

TABLE 9

Describes 3 compounds of formula (I-9) below, wherein $A_1$, $R^6$ and $Z^1$ to $Z^5$ are as specified.

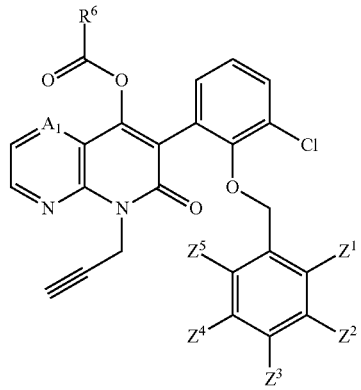

(I-9)

| Compound | $A_1$ | $R^6$ | $Z^1$ | $Z^2$ | $Z^3$ | $Z^4$ | $Z^5$ | NMR data |
|---|---|---|---|---|---|---|---|---|
| 9.001 | CH | $^i$Pr | H | H | H | H | H | (CDCl$_3$) 8.71 (1H, dd) 7.74 (1H, dd) 7.47 (1H, dd 7.8) 7.23 (1H, dd) 7.16 (4H, m) 7.06 (3H, m) 5.24 (2H, qd) 5.05 (1H, d) 4.84 (1H, d) 2.66 (1H, spt) 2.13 (1H, t) 1.09 (3H, d) 1.03 (3H, d). |
| 9.002 | C—OMe | Me | H | H | H | H | H | |
| 9.003 | N | $^i$Pr | H | H | H | H | H | (CDCl$_3$) 8.59 (1H, d) 8.48 (1H, d) 8.49 (1H, dd) 7.16 (4H, m) 7.04 (3H, m) 5.16 (1H, dd) 5.08 (1H, dd) 4.99 (2H, m) 2.77 (1H, spt) 2.15 (1H, t) 1.17 (3H, d) 1.12 (3H, d). |

TABLE 10

Describes 3 compounds of formula (I-10) below, wherein $A_1$ and $Z^1$ to $Z^5$ are as specified.

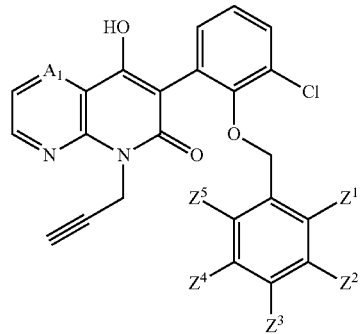

(I-10)

| Compound | $A_1$ | $Z^1$ | $Z^2$ | $Z^3$ | $Z^4$ | $Z^5$ | NMR data |
|---|---|---|---|---|---|---|---|
| 10.001 | CH | H | H | H | H | H | (CDCl$_3$) 8.70 (1H, dd) 8.28 (1H, dd) 7.52 (3H, m) 7.17 (7H, m) 5.30 (2H, d) 5.15 (1H, br. s.) 4.54 (1H, m) 2.17 (1H, t). |
| 10.002 | C—OMe | H | H | H | H | H | |
| 10.003 | N | H | H | H | H | H | (CDCl$_3$) 8.66 (1H, d) 8.41 (1H, d) 7.86 (1H, br. s) 7.50 (1H, dd) 7.27 (1H, dd) 7.18 (1H, t) 7.14 (2H, m) 6.97 (3H, m) 5.14 (2H, dq) 5.02 (1H, d) 4.94 (1H, d) 2.16 (1H, t) |

TABLE 11

Describes 3 compounds of formula (I-11) below, wherein $A_1$, $R^6$ and $Z^1$ to $Z^5$ are as specified.

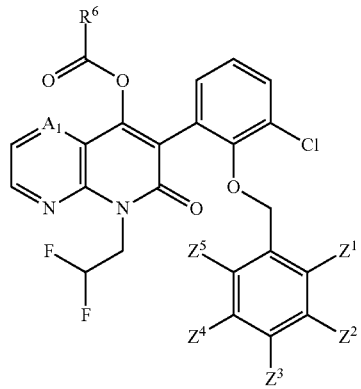

(I-11)

| Compound | $A_1$ | $R^6$ | $Z^1$ | $Z^2$ | $Z^3$ | $Z^4$ | $Z^5$ | NMR data |
|---|---|---|---|---|---|---|---|---|
| 11.001 | CH | $^i$Pr | H | H | H | H | H | (CDCl$_3$) 8.65 (1H, dd) 7.76 (1H, dd) 7.48 (1H, dd) 7.25 (1H, dd) 7.11 (7H, m) 6.20 (1H, m) 5.04 (1H, d) 4.88 (3H, m) 2.67 (1H, spt) 1.10 (3H, d) 1.04 (3H, d). |
| 11.002 | C—OMe | Me | H | H | H | H | H | |
| 11.003 | N | $^i$Pr | H | H | H | H | H | (CDCl$_3$) 8.54 (1H, d) 8.50 (1H, d) 7.50 (1H, quin) 7.15 (4H, m) 7.05 (3H, m) 6.11 (1H, tt) 4.98 (2H, m) 4.77 (2H, m) 2.78 (1H, spt) 1.18 (3H, d) 1.13 (3H, d). |

TABLE 12

Describes 3 compounds of formula (I-12) below, wherein $A_1$ and $Z^1$ to $Z^5$ are as specified.

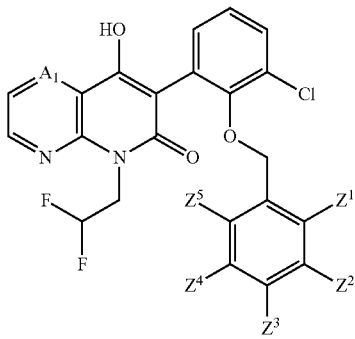

(I-12)

| Compound | $A_1$ | $Z^1$ | $Z^2$ | $Z^3$ | $Z^4$ | $Z^5$ | NMR data |
|---|---|---|---|---|---|---|---|
| 12.001 | CH | H | H | H | H | H | (CDCl$_3$) 8.63 (1H, dd) 8.29 (1H, dd) 7.50 (2H, m) 7.24 (2H, m) 7.11 (5H, m) 6.29 (1H, m) 4.94 (4H, m). |
| 12.002 | C—OMe | H | H | H | H | H | |
| 12.003 | N | H | H | H | H | H | (CDCl$_3$) 8.62 (1H, d) 8.43 (1H, d) 7.93 (1H, br. s) 7.51 (1H, dd) 7.25 (1H, m) 7.19 (1H, t) 7.08 (2H, m) 6.97 (3H, m) 6.17 (1H, tt) 4.97 (2H, q) 4.78 (2H, m). |

BIOLOGICAL EXAMPLES

B1 Post-emergence Efficacy

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-

5). Compounds are applied at 1000 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are shown below in Table 13, on a five point scale (5=80-100%; 4=60-79%; 3=40-59%; 2=20-39%; 1=0-19%).

TABLE 13

Control of weed species by compounds of formula (I) after post-emergence application at a rate of 1000 g/Ha

| Compound | SOLNI | AMARE | SETFA | ALOMY | ECHCG | IPOHE |
|---|---|---|---|---|---|---|
| 1.001 | 5 | 5 | 4 | 2 | 4 | 5 |
| 1.003 | 5 | 5 | 3 | 1 | 4 | 5 |
| 1.004 | 5 | 5 | 1 | 1 | 3 | 3 |
| 1.007 | 4 | 4 | 1 | 1 | 1 | 1 |
| 1.008 | 5 | 5 | 5 | 5 | 5 | 5 |
| 2.001 | 5 | 5 | 5 | 5 | 5 | 5 |
| 2.002 | 5 | 4 | 5 | 5 | 5 | 5 |
| 2.003 | 5 | 5 | 4 | 3 | 5 | 5 |
| 2.004 | 5 | 5 | 4 | 4 | 4 | 5 |
| 2.006 | 5 | 5 | 5 | 4 | 5 | 5 |
| 2.008 | 5 | 5 | 5 | 5 | 5 | 5 |
| 3.001 | 5 | 5 | 1 | 2 | 2 | 5 |
| 3.003 | 5 | 5 | 1 | 1 | 1 | 5 |
| 3.004 | 5 | 4 | 1 | 1 | 1 | 5 |
| 3.006 | 5 | 5 | 1 | 1 | 1 | 5 |
| 3.007 | 2 | 4 | 1 | 1 | 1 | 2 |
| 3.008 | 5 | 5 | 5 | 4 | 5 | 5 |
| 4.001 | 5 | 5 | 1 | 4 | 4 | 5 |
| 4.003 | 5 | 5 | 1 | 1 | 2 | 5 |
| 4.004 | 5 | 5 | 1 | 2 | 2 | 5 |
| 4.005 | 5 | 5 | 1 | 1 | 1 | 5 |
| 4.006 | 5 | 5 | 2 | 2 | 2 | 5 |
| 4.007 | 5 | 5 | 2 | 3 | 3 | 5 |
| 4.008 | 5 | 5 | 5 | 4 | 5 | 5 |
| 5.001 | 5 | 5 | 2 | 1 | 3 | 5 |
| 5.003 | 5 | 5 | 5 | 2 | 2 | 5 |
| 6.001 | 5 | 5 | 2 | 3 | 4 | 5 |
| 6.002 | 5 | 5 | 5 | 5 | 5 | 5 |
| 6.003 | 5 | 5 | 5 | 4 | 4 | 5 |
| 7.001 | 5 | 5 | 1 | 1 | 1 | 5 |
| 7.002 | 5 | 5 | 5 | 4 | 5 | 5 |
| 7.003 | 5 | 5 | 5 | 2 | 2 | 5 |
| 8.001 | 5 | 5 | 1 | 3 | 3 | 5 |
| 8.002 | 5 | 5 | 4 | 4 | 4 | 5 |
| 8.003 | 5 | 5 | 5 | 3 | 4 | 5 |
| 9.001 | 5 | 3 | 1 | 1 | 2 | 5 |
| 9.003 | 5 | 4 | 5 | 2 | 5 | 5 |
| 10.001 | 5 | 4 | 1 | 1 | 1 | 5 |
| 10.003 | 5 | 5 | 5 | 4 | 5 | 5 |
| 11.001 | 5 | 5 | 1 | 1 | 1 | 5 |
| 11.003 | 5 | 5 | 5 | 2 | 5 | 5 |
| 12.001 | 5 | 5 | 1 | 1 | 1 | 5 |
| 12.003 | 5 | 5 | 5 | 2 | 5 | 5 |

The invention claimed is:
1. A compound of formula (I)

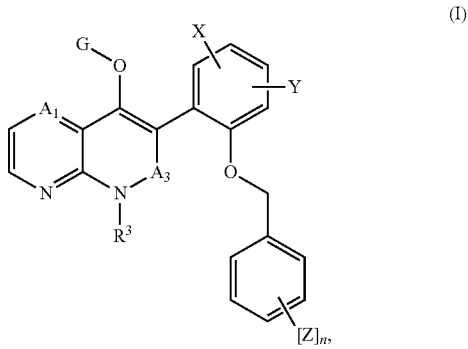

or a salt or N-oxide thereof,
wherein $A_1$ is N or $CR^1$;
$R^1$ is hydrogen, $C_1$-$C_4$alkyl, $C_1$-$C_3$haloalkyl, $C_1$-$C_4$alkoxy, $C_1$-$C_4$alkylthio, halogen, cyano, hydroxyl, or phenyl optionally substituted by one to five $R^4$ which may be the same or different;
$A_3$ is C(O) or S(O)$_2$;
G is hydrogen, or C(O)$R^6$;
X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;
n is an integer of 0, 1, 2, 3, 4, or 5;
each Z is independently $C_1$-$C_3$ alkyl, $C_1$-$C_3$ alkoxy, $C_1$-$C_3$haloalkyl, $C_1$-$C_3$haloalkoxy, or halogen;
$R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N-$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$$C_6$alkyl- or aryl-$C_1$-$C_6$alkyl- wherein the aryl moiety is substituted by one to three $R^{10}$, which may be the same or different, or heterocyclyl-$C_1$-$C_6$alkyl- or heterocyclyl-$C_1$-$C_6$alkyl- wherein the heterocyclyl moiety is substituted by one to three $R^{10}$, which may be the same or different;
each $R^4$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, or $C_1$-$C_{10}$alkylcarbonylamino-;
$R^6$ is selected from the group consisting of $C_1$-$C_6$alkyl, $C_1$-$C_6$alkenyl, $C_1$-$C_6$alkynyl, $C_1$-$C_6$alkyl-S—, —NR$^7$R$^8$ and phenyl optionally substituted by one or more $R^9$;
$R^7$ and $R^8$ are independently selected from the group consisting of $C_1$-$C_6$ alkyl and $C_1$-$C_6$ alkoxy, or $R^7$ and $R^8$ together can form a morpholinyl ring; and,
$R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and each $R^{10}$ is independently halo, $C_1$-$C_4$alkyl, $C_1$-$C_4$haloalkyl, $C_1$-$C_4$alkoxy or $C_1$-$C_4$haloalkoxy.

2. The compound of claim 1, wherein G is hydrogen, or $C(O)R^6$ wherein $R^6$ is isopropyl.

3. The compound of claim 1, wherein $R^3$ is propargyl or difluoroethyl.

4. The compound of claim 1 wherein X is hydrogen or halogen.

5. The compound of claim 1 wherein Y is hydrogen, $C_1$-$C_3$ alkyl, $C_1$-$C_3$haloalkyl, or halogen.

6. The compound according to claim 1 wherein X is ortho with respect to the bi-cyclic moiety.

7. The compound according to claim 1 wherein Y is ortho with respect to the benzyloxy moiety.

8. The compound according to claim 1 wherein $A_3$ is $C(O)$.

9. The compound according to claim 1 wherein $R^1$ is selected from the group consisting of hydrogen, halogen, $C_1$-$C_3$alkyl and $C_{1-3}$alkoxy.

10. The compound according to claim 1 wherein n is 0, 1, or 2.

11. The compound according to claim 1 wherein each Z is independently selected from halogen, methyl, methoxy, and trifluoromethyl.

12. A herbicidal composition comprising a herbicidal compound according to claim 1 and an agriculturally acceptable formulation adjuvant.

13. A herbicidal composition according to claim 12, further comprising at least one additional pesticide.

14. A method of controlling unwanted plant growth, comprising applying a compound of formula (I) as defined in claim 1 to the unwanted plants or to the locus thereof.

* * * * *